(12) United States Patent
Hegland

(10) Patent No.: US 8,702,635 B2
(45) Date of Patent: Apr. 22, 2014

(54) PHALANGEAL DEFORMITY RING SPLINT

(76) Inventor: June M. Hegland, St. Louis Park, MN (US)

( * ) Notice: Subject to any disclaimer, the term of this patent is extended or adjusted under 35 U.S.C. 154(b) by 42 days.

(21) Appl. No.: 13/284,266

(22) Filed: Oct. 28, 2011

(65) Prior Publication Data

US 2012/0289877 A1 Nov. 15, 2012

Related U.S. Application Data

(63) Continuation-in-part of application No. 13/107,453, filed on May 13, 2011, now Pat. No. 8,585,625.

(51) Int. Cl.
*A61F 5/00* (2006.01)

(52) U.S. Cl.
USPC .................................................. 602/22

(58) Field of Classification Search
USPC .......... 602/5, 12, 22, 30; 128/878–880; 5/623
See application file for complete search history.

(56) References Cited

U.S. PATENT DOCUMENTS

| | | | | | |
|---|---|---|---|---|---|
| 440,434 | A | * | 11/1890 | Mocarty | 602/30 |
| 1,561,631 | A | * | 11/1925 | Winter | 128/880 |
| 1,733,933 | A | * | 10/1929 | Beltz | 128/880 |
| 3,170,460 | A | * | 2/1965 | Stilson | 602/22 |
| 4,243,026 | A | * | 1/1981 | Barber | 602/22 |
| 4,270,528 | A | * | 6/1981 | Hanson | 602/22 |
| 4,441,489 | A | * | 4/1984 | Evans et al. | 602/22 |
| 4,932,396 | A | * | 6/1990 | Garris | 602/22 |
| 5,012,799 | A | * | 5/1991 | Remmen | 602/30 |
| 5,020,524 | A | * | 6/1991 | Donohue | 602/22 |
| 5,376,091 | A | * | 12/1994 | Hotchkiss et al. | 606/55 |
| 5,681,269 | A | * | 10/1997 | Basaj et al. | 602/22 |
| 5,730,154 | A | * | 3/1998 | DeRidder | 128/880 |
| 5,848,983 | A | * | 12/1998 | Basaj et al. | 602/22 |
| 6,110,136 | A | * | 8/2000 | Belkin | 602/22 |
| 8,235,928 | B2 | * | 8/2012 | Padova | 602/22 |
| 8,262,599 | B2 | * | 9/2012 | Chandrasekar et al. | 602/20 |
| 2002/0129619 | A1 | | 9/2002 | Wolff | |
| 2006/0094989 | A1 | * | 5/2006 | Scott et al. | 601/5 |
| 2007/0017252 | A1 | | 1/2007 | Yoshida et al. | |
| 2009/0099493 | A1 | | 4/2009 | Barnes | |
| 2009/0326428 | A1 | | 12/2009 | Farrell et al. | |

OTHER PUBLICATIONS

Jessica, Ring O Blog, "Sterling Silver Filigree Armor Ring," http://ringoblog.com/ring-by-type/sterling-silver-rings/sterling-silver-filigree-ring/, Sep. 10, 2010 (1 page).

* cited by examiner

*Primary Examiner* — Patricia Bianco
*Assistant Examiner* — Raymond E Harris
(74) *Attorney, Agent, or Firm* — Allison Johnson; Allison Johnson, P.A.

(57) ABSTRACT

A ring splint that includes a first loop, a second at least partial loop, an elongated support and optionally a third at least partial loop, the first loop and the second at least partial loops being attached to the elongated support such that the elongated support contacts the ventral surface (e.g., palmar or plantar) of a phalange (e.g., finger or toe) when in position on a phalange.

19 Claims, 7 Drawing Sheets

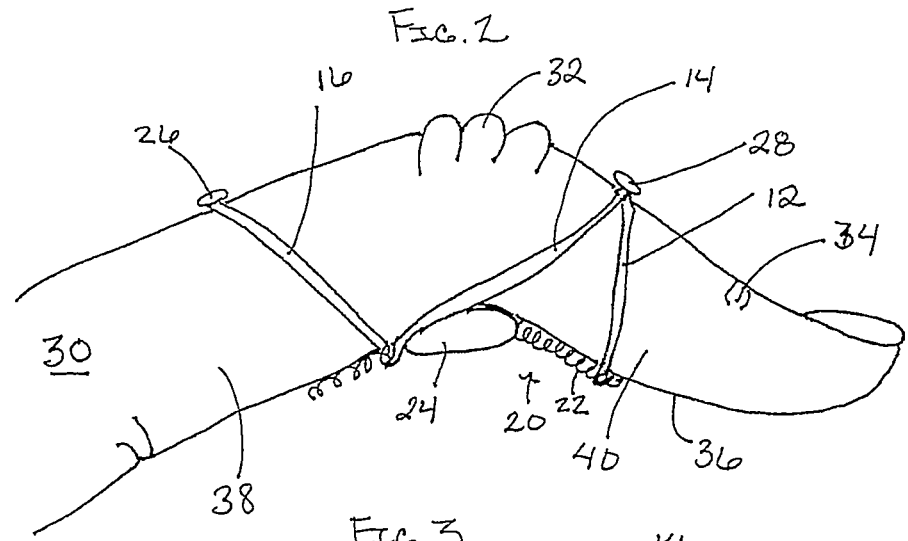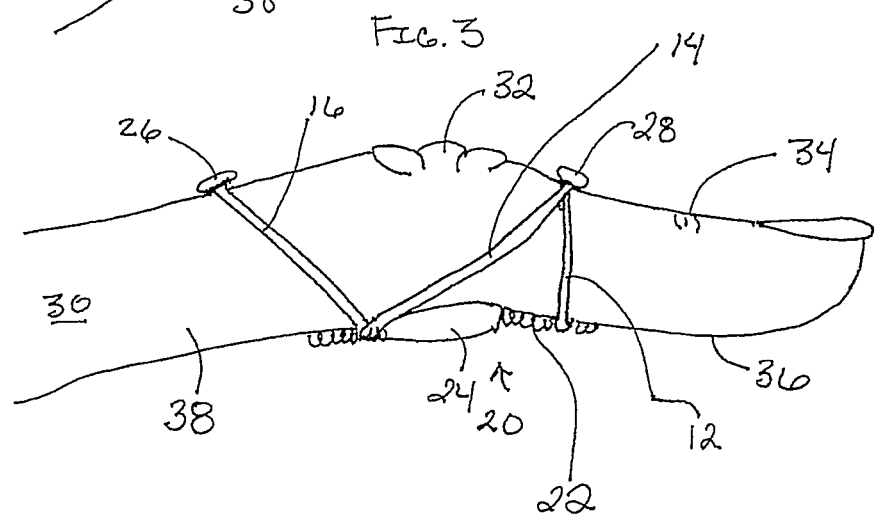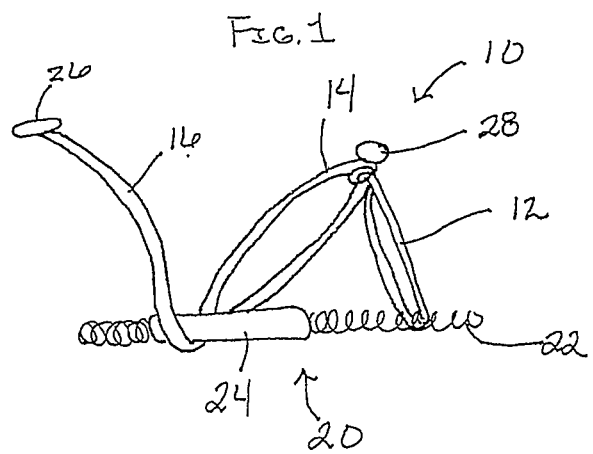

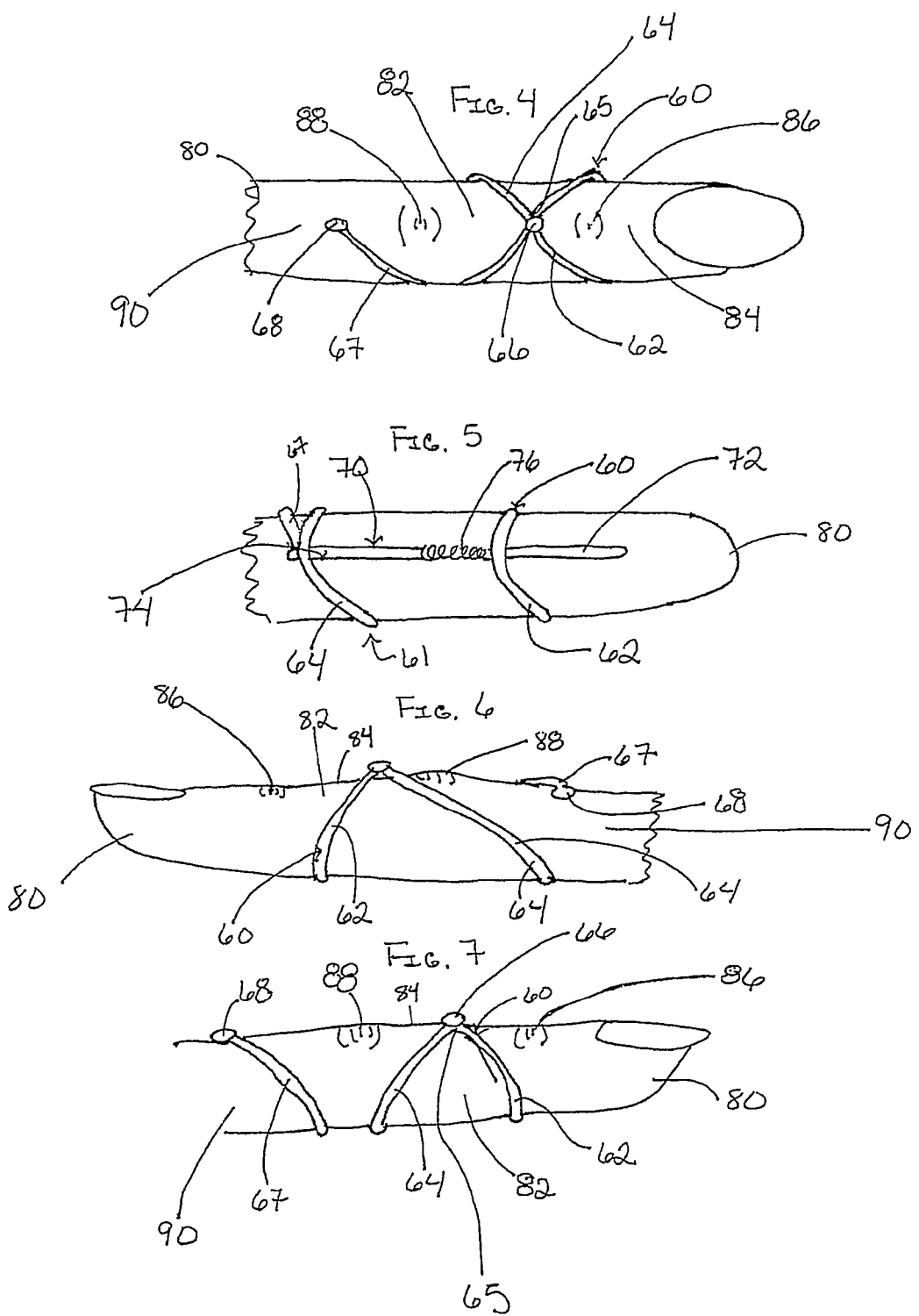

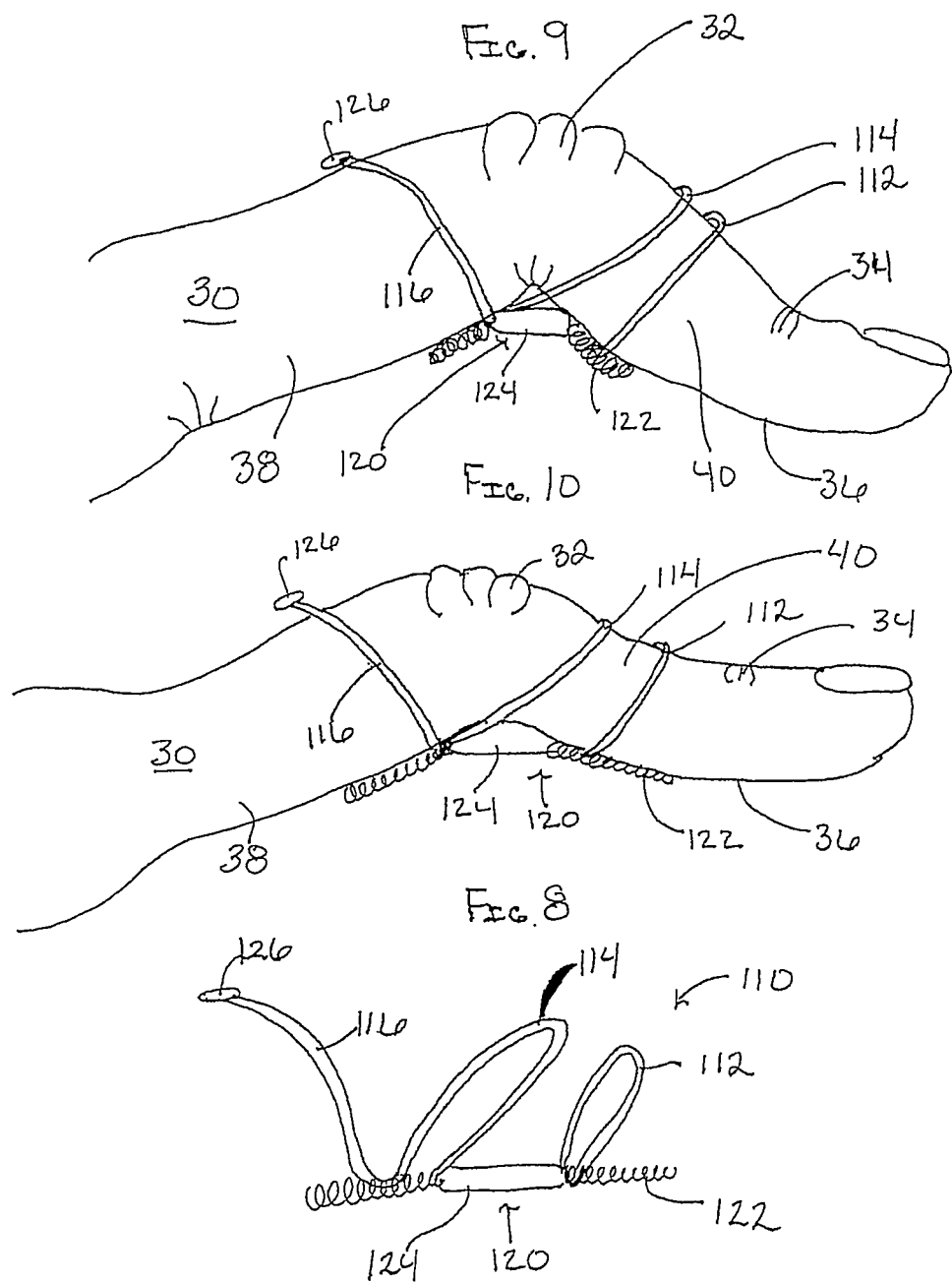

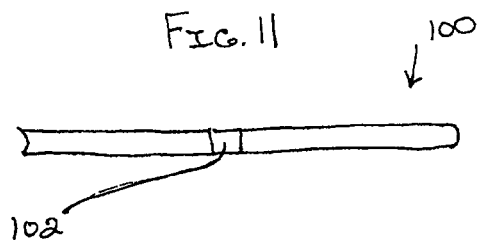
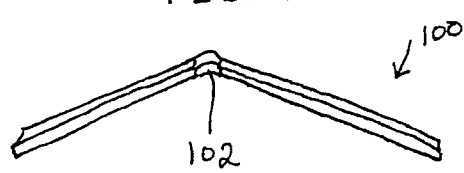
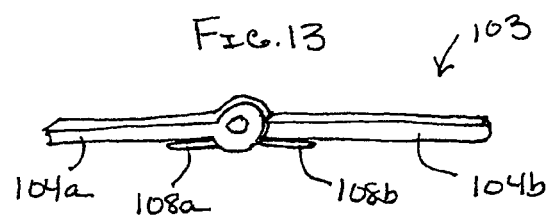
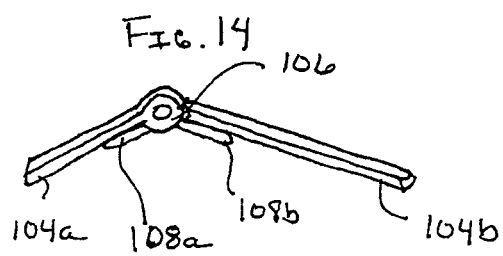

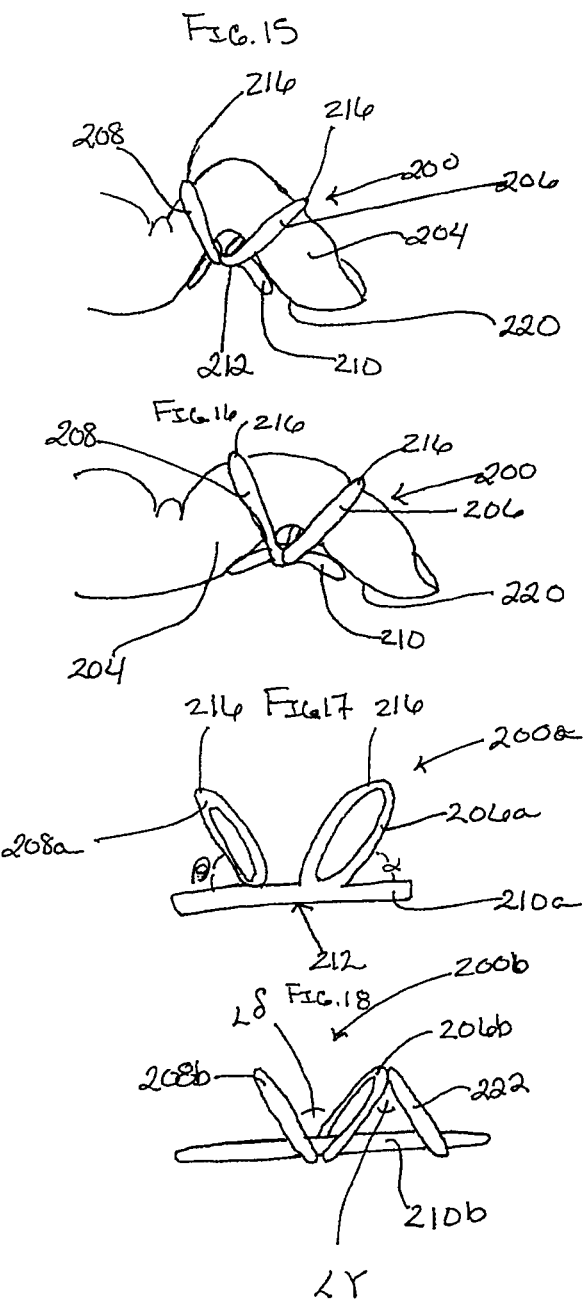

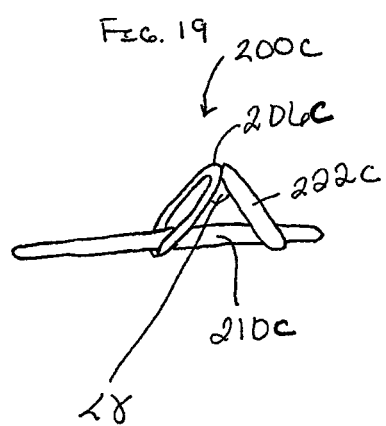

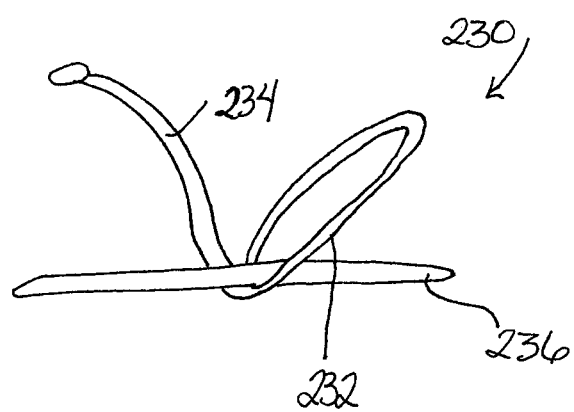

PHALANGEAL DEFORMITY RING SPLINT

CROSS-REFERENCE TO RELATED APPLICATIONS

This application is a continuation-in-part of U.S. patent application Ser. No. 13/107,453, filed May 13, 2011, and is incorporated herein.

BACKGROUND

The invention relates to applying an extension force to a phalangeal deformity.

Phalangeal deformities occur in fingers and toes. In fingers, one such deformity is referred to as a "boutonniere deformity." In toes, one such deformity is referred to as a "hammer toe."

Boutonniere deformities occur in fingers and consist of a proximal interphalangeal joint that is flexed and a distal interphalangeal joint that is hyperextended. This deformity makes it difficult or impossible to extend the proximal interphalangeal joint. It is commonly caused by injury or by an inflammatory condition like rheumatoid arthritis.

A pseudoboutonniere deformity is a condition marked by proximal interphalangeal joint flexion contracture and restricted flexion of the distal interphalangeal joint. The characteristic hyperextension of the distal interphalangeal in boutonniere deformities is not present in pseudoboutonniere deformities.

Ring splints have been developed to straighten or realign interphalangeal joints of fingers and thumbs. One such ring splint includes two elliptical rings joined by an elliptical spacer as described in U.S. Pat. No. 4,932,396. The ring splint disclosed in U.S. Pat. No. 4,932,396 is described as being worn with the spacer over the joint on a boutonniere finger or mallet finger. In such a position, the ring splint is described as being capable of holding the finger in extension.

Hammer toe is a deformity of the toe in which the end of the toe bends downward in a claw-like position. Hammer toe affects the proximal interphalangeal joint of the toes. Mallet toe is also a deformity of the toe that affects the distal interphalangeal joint. Claw toe, another deformity of the toe, is the presence of dorsiflexion of the proximal phalanx on the lesser metatarsophalangeal in combination with flexion of both the proximal and distal interphalangeal joints.

There are various ways that one can attempt to address toe deformities including wearing the proper size shoes and avoiding wearing high heels. In severe cases surgery is necessary to correct the deformity. The surgery can involve cutting or moving tendons and ligaments. Sometimes the bones on each side of the joint need to be connected (fused) together.

SUMMARY

In another aspect, the invention features a ring splint that includes a first loop, a second loop attached to the first loop and extending at an angle from the first loop, and an elongated support attached to the first loop at a first area of attachment and the second loop at a second area of attachment, the elongated support including a longitudinal extent extending beyond the first and second areas of attachment, the elongated support being positioned relative to the loops such that the elongated support contacts the ventral surface of a phalange when the ring splint is in position on a phalange.

In some embodiments, the elongated support exhibits a rigid property. In one embodiment, the elongated support also exhibits a flexible property.

In another embodiment, the ring splint further includes a third at least a partial loop. In one embodiment, the third at least a partial loop is attached to the second loop. In some embodiments, the third at least a partial loop defines an angle with the second loop that is greater than 30 degrees. In other embodiments, the third at least a partial loop is attached to the support. In another embodiment, the third at least a partial loop extends from the second loop in the form of a spiral.

In some embodiments, the first loop extends from the support and defines an angle with the support that is less than 90 degrees. In other embodiments, the second loop extends from the support and defines an angle with the support that is less than 90 degrees.

In another embodiment, when the ring splint is positioned on a toe such that the elongated support is in contact with the plantar surface of the toe, the elongated support maintains the toe in at least partial extension.

In other embodiments, the ring splint further includes a third at least partial loop attached to the second loop and extending away from the second loop at an angle of at least 10 degrees.

In one embodiment, the support includes a hinge. In other embodiments, the support includes at least one of a living hinge and a spring hinge. In some embodiments, the support includes a spring. In another embodiment, the support includes a spring that includes a first end and a second end, a first elongate section attached to the first end of the spring, and a second elongate section attached to the second end of the spring.

In other embodiments, the support further includes a cushion enveloping at least a portion of the longitudinal extent. In another embodiment, the support is removably attached to the first and second loops. In some embodiments, the support is repeatedly repositionable on the first and second loops.

In another embodiment, the ring splint further includes an ornamental component attached to at least one of the first loop and the second loop.

In one embodiment, the second loop extends at an angle of at least 10 degrees from the first loop.

In another aspect, the invention features a ring splint that includes a first loop, a second at least partial loop extending away from the first loop at an angle that is at least 45 degrees, and an elongated support attached to the first loop and the second loop forming at least one area of attachment, the elongated support comprising a longitudinal extent extending beyond the at least one area of attachment, the first loop and second loop being positioned relative to the elongated support such that when the ring splint is in position on a toe, the elongated support contacts the plantar surface of the toe. In one embodiment, the second at least partial loop is a closed loop and is flexible. In some embodiments, the second at least partial loop extends from the first loop in the form of a spiral.

In other aspects the invention features a method of using a ring splint described herein, the method including positioning a first loop of the ring splint around the intermediate phalanx of a phalange, positioning a second loop of the ring splint around the intermediate phalanx of a phalange, and positioning the elongated of the support ring splint against at least a portion of a ventral surface of the phalange. In one embodiment, the method includes positioning a third loop of the ring splint around the proximal phalanx of a phalange, positioning the first loop around the intermediate phalanx of the phalange, positioning the second loop around the intermediate phalanx of the phalange, and positioning the elongated support against at least a portion of a ventral surface of the phalange.

In another aspect, the invention features a method of using a ring splint described herein wherein the method includes positioning the second loop of the ring splint around the proximal phalanx of a phalange, positioning the first loop of the ring splint around the intermediate phalanx of the phalange, and positioning the elongated support against at least a portion of a ventral surface of the phalange.

In another aspect, the invention features a ring splint that includes a first loop, a second loop, a third at least partial loop, and an elongated support, the first loop and the second loop being attached to the support, the elongated support exhibiting a rigid property and a flexible property, such that the elongated support maintains a finger in at least partial extension when the ring is on a finger and the elongated support is in contact with the palmar surface of the finger, and flexes when the user bends the finger. In one embodiment, the second loop terminates in the third at least partial loop. In another embodiment, the first loop is attached to the second loop.

In some embodiments, the support includes a hinge. In one embodiment, the support includes at least one of a living hinge and a spring hinge.

In other embodiments, the support includes a spring. In one embodiment, the support includes a spring that includes a first end, a first elongate section attached to the first end of the spring, and a second elongate section attached to the second end of the spring.

In another embodiment, the support includes a longitudinal extent and a cushion enveloping at least a portion of the longitudinal extent.

In some embodiments, the support is removably attached to the first and second loops. In other embodiments, the support is repeatedly repositionable within the first and second loops.

In another embodiment, the ring is in position on the finger the support is positioned between the palmar surface of the finger and the first and second loops.

In other embodiments, the ring splint further includes an ornamental component. In another embodiment, the ring splint further includes an ornamental component on at least one of the second loop and the third at least partial loop.

In another embodiment, the ring splint includes a first loop, a second loop, the first loop being attached to the second loop, a third at least partial loop, and an elongated support attached to the first and second loops and exhibiting rigid properties and flexible properties such that the elongated support maintains a finger in at least partial extension when the splint is in position on a finger and flexes when the user bends the finger.

In other aspects, the invention features method of using the ring splint of claim 1, the method including positioning the third at least partial loop around a portion of the proximal phalanx of a finger, positioning the second loop around the intermediate phalanx, positioning the first loop around the intermediate phalanx, and positioning the elongated support against at least a portion of the palmar surface of the finger.

In another aspect, the invention features a finger ring that includes a first loop, a second loop, and a third at least partial loop, the first loop and the second loop being attached to one another at a first location, the third loop extending from the second loop, such that when the ring is positioned on a finger, the first loop loops around the intermediate phalanx of the finger, the second loop loops around the intermediate phalanx of the finger, the third at least partial loop loops around a portion of the proximal phalanx of the finger and the first location is positioned on the dorsal surface of the intermediate phalanx of the finger. In one embodiment, the third at least partial loop forms a spiral with the second loop. In other embodiments, the third at least partial loop is attached to the second loop.

When worn on a finger, the ring exerts a force against the finger that works to straighten (i.e., extend) the finger but also allows the finger to bend against the force when desired, e.g., when the user desires to grasp an item. The ring is particularly well-suited to being positioned on a finger that has a boutonniere deformity.

The ring also can be constructed to be aesthetically pleasing to the user.

Other features and advantages will be apparent from the following description of the drawings and the preferred embodiments, and from the claims.

BRIEF DESCRIPTION OF THE DRAWINGS

FIG. 1 is a perspective view of a ring splint according to one embodiment.

FIG. 2 is a perspective view of the ring splint of FIG. 1 positioned on a finger that has a boutonniere deformity where the finger is in a flexed position.

FIG. 3 is a perspective view of the ring splint of FIG. 1 positioned on a finger that has a boutonniere deformity where the finger is in a relatively extended position.

FIG. 4 is a top plane view of one embodiment of a finger ring positioned on a finger of a user where the finger is in extension.

FIG. 5 is a perspective view of a ring splint according to another embodiment.

FIG. 6 is a plane view of the first side of the finger ring of FIG. 4.

FIG. 7 is a plane view of the second side of the finger ring of FIG. 4.

FIG. 8 is a perspective view of a ring splint according to another embodiment.

FIG. 9 is a perspective view of the ring splint of FIG. 8 positioned on a finger that has a boutonniere deformity where the finger is in a flexed position.

FIG. 10 is a perspective view of the ring splint of FIG. 8 positioned on a finger that has a boutonniere deformity where the finger is in a relatively extended position.

FIG. 11 is a top view of a splint according to one embodiment.

FIG. 12 is a perspective view of the splint of FIG. 11.

FIG. 13 is a perspective view of a splint according to another embodiment.

FIG. 14 is a perspective view of the splint of FIG. 13 in a bent position.

FIG. 15 is a perspective view of a ring splint according to another embodiment positioned on a hammer toe.

FIG. 16 is a perspective view of the ring splint of FIG. 15 in which the toe is in a partially extended position.

FIG. 17 is a perspective view of a ring splint according to another embodiment.

FIG. 18 is a perspective view of a ring splint according to another embodiment.

FIG. 19 is a perspective view of a ring splint according to another embodiment.

FIG. 20 is a perspective view of a ring splint according to another embodiment.

GLOSSARY

In reference to the invention, these terms have the meanings set forth below:

The term "finger" includes all digits of the hand including the thumb.

The term "boutonniere deformity" as used herein refers to a boutonniere deformity and a pseudoboutonniere deformity.

The terms "phalange deformity" and "phalangeal deformity" as used herein refer to any deformity of a phalange.

The term "ventral" in reference to a phalange refers to the palmar surface when the phalange is a finger and the planter surface when the phalange is a toe.

DETAILED DESCRIPTION

The ring splint includes a first loop, a second loop, an elongated support, and an optional third at least partial loop, and. The first loop is dimensioned to be capable of being positioned around the intermediate phalanx of the finger of a user, e.g., the person wearing the ring. The second loop is also dimensioned to be capable of being positioned around the intermediate phalanx of the finger of the user. The third loop at least partial loop is dimensioned to be capable of being positioned around a portion of the proximal phalanx of the finger of the person wearing the ring, i.e., the user, preferably it is dimensioned to be positionable about the proximal phalanx of a finger that exhibits a boutonniere deformity. For ease of reference, an at least partial loop will sometimes be referred to herein as a loop. At least one of the first loop, the second loop and the third loop is connected to the elongated support to hold the support against the palmar surface of the finger when the ring splint is worn on a finger.

The elongated support is sufficiently rigid and is associated with the loops in such a way that when the splint is in position on a finger, the support exerts a force against the palmar surface of the finger. The force prevents the finger from flexing (i.e., bending) until such time as the user desires to flex the finger. The elongated support acts in combination with the loops to provide a corrective action against the finger, i.e., applies an extension force against the palmar surface of the finger. The support thus exerts a force against the palmar surface of the finger that encourages the finger to extend. In the case of a finger that exhibits a boutonniere deformity, the support exerts a force on the finger that encourages the finger to extend from its normally flexed position. The support is also sufficiently flexible (e.g., in the area of the interphalangeal joint) so as to allow the finger to flex when the user flexes his or her finger.

Referring to FIG. 1, a finger ring splint 10 that includes a first loop 12, a second loop 14, a partial loop 16, and an elongated support 20 in the form of a spring 22, is shown. A foam cushion 24 surrounds the mid-section of the spring 22 to provide a surface that is comfortable to the user. The first loop 12, the second loop 14, and the partial loop 16 are attached to the elongated support 20. The first loop 12 and the second loop 14 of the ring 10 wrap around the support 20 which helps to maintain the support 20 in a snug position against the palmar surface of a finger. The second loop 14 is part of a spiral loop that terminates in the partial loop 16. The second loop 14 spirals around the elongated support 20 and assists in maintaining the support 20 in a desired position on the finger 30. The dimensions of the loops and the support 20 assist in pulling the support 20 against the palmar surface of the finger 30. The partial loop 16 enables the ring 10 to be relatively easily positioned over the proximal interphalangeal joint (PIP) of a finger.

A first decorative element 26 is positioned on the end of the partial loop 16 to provide an aesthetically pleasing appearance. A second decorative element 28 is positioned at the union between the first loop 12 and the second loop 14 to provide an aesthetically pleasing appearance.

Referring to FIGS. 2 and 3, the finger ring 10 is positioned on a finger 30 that has a boutonniere deformity. The first loop 12 and the second loop 14 are positioned between the proximal interphalangeal joint 32 and the distal interphalangeal joint 34 and around the intermediate phalanx 40, and the third partial loop is positioned about a portion of the proximal phalanx 38. The support 20 extends along the palmar surface 36 of the finger 30 and contacts the palmar surfaces of the proximal phalanx 38 and the intermediate phalanx 40 and exerts a force on the palmar surfaces the finger encouraging the finger 30 to achieve an extended position. In FIG. 2, the finger 30 is in a relatively more flexed position and the elongated support 20 is in a relatively non-linear position. In FIG. 3, the finger 30 is in an extended position and the elongated support 20 is in a relatively more linear position.

Other embodiments are within the claims. FIGS. 4, 6 and 7, for example, illustrate a finger ring 60 that includes a first loop 62, a second loop 64, and a third partial loop 67, in position on a finger 80 that is in an extended position. The first and second loops 62, 64 loop around the intermediate phalanx 82 of the finger. The first and second loops 62, 64 are affixed together at a union 65 that, when the ring is worn, is positioned on the dorsal surface 84 of the finger 80 between the distal interphalangeal joint 86 and the intermediate interphalangeal joint 88. A first decorative element 66 is positioned at the union 65 between the first and second loops 62, 64. The third partial loop 67 wraps around a portion of the proximate phalanx 90 and terminates in a second decorative element 68. The finger ring 60 can be worn with or without a support.

FIG. 5 illustrates an embodiment of the ring 60 that is in the form of a ring splint 61 that includes an elongated linear support 70 positioned between the first loop 62 and the second loop 64. The elongated support 70 includes a first end portion 72, a second end portion 74, and a middle portion 76. The first and second end portions 72, 74 are of a rigid material and in the form of thin elongated reeds, and the middle portion 76 is a spring. The first and second end portions 72, 74 are attached to the spring 76. A cushion (not shown) optionally surrounds the spring 76 and a portion of the first and second end portions 72, 74 to create more comfort to the user of the ring 60.

FIGS. 8-10 illustrate a ring splint 110 that includes a first loop 112, a second loop 114, a partial loop 116, and an elongated support 120 in the form of a spring 122. A foam cushion 124 surrounds the mid-section of the spring 122 to provide a surface that is comfortable to the user. The first loop 112, the second loop 114, and the partial loop 116 are attached to the elongated support 120. The first loop 112 and the second loop 114 of the ring 110 wrap around the support 120, which helps to maintain the support 120 in a snug position against the palmar surface 36 of a finger 30. The second loop 114 is part of a spiral loop that includes the second loop 114 and terminates in the partial loop 116. The second loop 114 spirals around the elongated support 120 and assists in maintaining the support 120 in a desired position on the finger 30. The dimensions of the loops and the support 120 assist in pulling the support 120 against the palmar surface of the finger 30. The partial loop 116 enables the ring 110 to be relatively easily positioned over the proximal interphalangeal joint 32 of a finger 30. The partial loop 116 includes a decorative element 126, e.g., a gem stone, attached to the terminal end thereof.

Referring to FIGS. 9 and 10, the ring splint 110 is positioned on a finger 30 that has a boutonniere deformity. The first loop 112 and the second loop 114 are positioned between the proximal interphalangeal joint 32 and the distal interphalangeal joint 34 and around the intermediate phalanx 40, and the third partial loop 116 is positioned about a portion of the proximal phalanx 38. The support 120 extends along the palmar surface 36 of the finger 30 and contacts the palmar surfaces of the proximal phalanx 38 and the intermediate phalanx 40 and exerts a force on the palmar surfaces the finger encouraging the finger 30 to achieve an extended position. In FIG. 9, the finger 30 is in a relatively more flexed and the elongated support 120 is in a relatively non-linear position. In FIG. 10, the finger 30 is in an extended position and the elongated support 120 is in a relatively more linear position.

The loops of the ring splint can be positioned (e.g., attached) relative to one another at a variety of angles such that they define an angle there between including, e.g., an angle of at least 10 degrees, at least 20 degrees, at least 30 degrees, at least 45 degrees, at least 60 degrees, or even at least 90 degrees. Each loop of the ring splint also can be positioned (e.g., attached) relative to the elongated support such that it defines a variety of angles with the elongated support including, e.g., an angle of at least 10 degrees, at least 20 degrees, at least 30 degrees, at least 45 degrees, less than 60 degrees, or even less than 90 degrees.

The loops of the ring splint can be in a variety of forms including, e.g., circular, spiral, elliptical, oval, and ovoid. The loops can be continuous (i.e., form a closed loop) or discontinuous (i.e., form a partial loop). The loops can be made from any material. The loop material can have a variety of properties including, e.g., being rigid, malleable, deformable, flexible, and combinations thereof. Useful loop materials include polymer (e.g., thermoset polymer, thermoplastic polymer, elastomer, rubber, and combinations thereof), composite (e.g., polymer and cellulose fiber composites, and polymer and metal (e.g., fibers, particles and fines)), metal, and combinations thereof. Suitable metals include, e.g., copper, gold, silver, aluminum, alloys, steel, iron, tin, and combinations thereof.

The elongated support can be of a variety of configurations and made from a variety of materials. The length of the support is selected to provide the support function to the finger while being comfortable to the user. Useful elongate supports include, e.g., springs, hinges, cylindrical tubes, cylindrical rods, cuboid (e.g., a rectangular paralellpiped), and combinations thereof. The ends and sides of the support can be rounded to provide comfort to the user. Useful hinged supports include, e.g., spring hinges, living hinges, hinges that include male and female components, and combinations thereof. The hinge preferably is positioned on the support and in relation to the loops such that it enables a finger to bend at its joint when the splint is in position on the finger and the user causes the finger to exert a bending force. The hinge can be positioned, for example, on the palmar surface of the inter-proximal joint.

Examples of useful supports include plastic splints that include an elongated member and a living hinge disposed along the elongated member and perpendicular to the longitudinal axis of the elongated member, and splints that include an elongated member having a longitudinal extent and a spring hinge disposed perpendicular to the longitudinal extent. The hinge is positioned at a location along the longitudinal extent of the support to facilitate bending.

FIGS. 11 and 12 illustrate one embodiment of a support 100 that is in the form of a polymeric, elongated member 100 that includes a living hinge 102.

In another embodiment, the support 103 includes two elongated members 104a, 104b joined together through a spring hinge 106, as illustrated in FIGS. 13 and 14. The ends 108a, 108b of the spring hinge 106 exert a force against the elongated members 104a, 104b, which pushes the elongated members 104a, 104b away from each other toward a more open, i.e., linear, position, as illustrated in FIG. 13. When in position on a finger, the flexing of the finger forces the elongated members 104a, 104b toward each other while the force of the spring exerts a countering force which creates resistance to the movement but does not prevent the flexing movement, as illustrated in FIG. 14.

The support is preferably an elongated element having a longitudinal extent. The support can be made from a variety of materials including, e.g., metal (e.g., alloys, stainless steel, spring steel, copper, gold, silver, tin, aluminum, and combinations thereof), polymer (e.g., thermoplastic polymers, thermoset polymers, thermoplastic elastomers, polyethylene, polypropylene, polyester, polystyrene, polyamide, elastomers (e.g., styrene-butadiene-rubber, styrene-isoprene-styrene, styrene-butadiene-styrene, styrene-ethylene-butene-styrene, styrene-ethylene-propene-styrene, silicone rubber and combinations thereof), composites (e.g., cellulose and polymer composites, and metal and polymer composites), wood, foam, and combinations thereof.

The support can be attached to the loops in a variety of configurations including, e.g., removably attached (i.e., the splint can be removed from the ring splint without damaging the ring) and permanently attached (i.e., removing the support would damage the ring). In one embodiment, the support is removably attached to at least one loop such that the support can easily slide into and out of position between the loops and the palmar surface of the finger. Removably attached supports can be configured to enable the support to be removed from the ring splint and replaced on the ring splint. Removable supports allow a user to replace the support with a relatively more rigid or less rigid support, and to replace the support when the support becomes soiled or worn.

The components (e.g., the loops, the support, the decorative components, and the cushion), of the ring can be attached to each other using any suitable mechanism including, e.g., mechanical devices, e.g., wires, fibers, staples, and clips, adhesive compositions (e.g., adhesive backed-tapes), welds (e.g., metal and polymer), snap fit mechanisms, friction fit mechanism, male-female connectors, and combinations thereof.

A protective element is optionally positioned on the support to protect the user from any pain or discomfort that might be caused by the support or movement of the support while it is in position on the finger. When the support includes a spring element, for example, the protective element can protect the user's skin from being pinched by the springs. The protective element can surround all or a portion of the support and can be positioned to provide comfort to the user. Useful protective elements include, e.g., the optional cushion described above, sleeves (e.g., a sleeve that at least partially or even completely surrounds a portion of the support (e.g., the skin contacting portion of the support), or even the entire support), and combinations thereof. Useful materials from which the protective element can be formed include, e.g., plastic (e.g., polymer films and coatings), elastomers (e.g., styrene-butadiene-rubber, styrene-isoprene-styrene, styrene-butadiene-styrene, styrene-ethylene-butene-styrene, styrene-ethylene-propene-styrene, rubber, ethylene propylene diene rubber, silicone rubber, and combinations thereof), foam (e.g., closed cell foam and open cell foam), cotton, gauze, adhesive tape (e.g., fibrous tape, medical tape, masking tape, painter's tape, and duct tape), and combinations thereof.

Although the third at least partial loop has been described and illustrated as a partial loop, in some embodiments it is in the form of a complete loop.

Although the ring splint has been described in reference to being positioned on a single finger, the splint and its components can be configured (e.g., dimensioned) to be positioned around more than one finger.

The elongate support can extend from the proximal phalanx to the intermediate phalanx, and optionally to the distal phalanx, from the intermediate phalanx to the distal phalanx, and combinations thereof. The ring can optionally include more than one elongate support and the elongate supports can be of the same or different construction, material, and dimensions relative to each other.

The decorative element can be of a variety of materials, shapes and sizes including, e.g., gem stone, metal, glass, flowers, geometric shapes, and combinations thereof.

Although the ring splints described herein have been described with respect to use on a finger or fingers, the ring splints described herein are also suitable for use on a toe or toes and can be dimensioned and constructed to be suitable for use on a toe(s) or finger(s). FIG. 15, for example, depicts a ring splint 200 in position on a hammer toe 204 that is in a flexed position. FIG. 16 depicts a ring splint 200 in position on a hammer toe 204 that is in a partially straightened position. The ring splint 200 includes a first loop 206, a second loop 208, an elongated support 210, a top 216 and a bottom 212. When worn by a user, the elongated support 210 of the ring splint 200 slides between the loops 206 and 208 and the plantar surface 220 of the toe 204.

In one embodiment, the loops 206a and 208a and the elongated support 210a of the ring splint 200a form a single unit as illustrated, for example, in FIG. 17. The loops 206a and 208a each form an angle, i.e., angles alpha (α) and beta (β), with the support 210a. In some embodiments, angles alpha and beta are less than 90 degrees.

In another embodiment, the loops 206b and 208b and the elongated support 210b of the ring splint 200b are made from at least one separable part as illustrated, for example, in FIG. 18. The loops 206b and 208b extend away from each other and define an angle there between, i.e., angle (δ), and loops 206b and 222 define an angle gamma (γ), there between. In some embodiments, angle delta is at least 30 degrees, at least 45 degrees, at least 60 degrees, and at least 90 degrees and angle gamma is less than 90 degrees or even at least 10 degrees.

In addition, although the ring splint has been described as including two loops and optionally a third at least partial loop, in some embodiments the ring splint includes one closed (e.g., continuous) loop and at least one partial (e.g., discontinuous) loop including, e.g., a closed loop and a partial loop or a closed loop and two partial loops. In some embodiments, the loops and partial loops are in the form of a spiral. The ring splint 200b of FIG. 18, for example, includes a first loop 206b, a second partial loop 208b, a third loop 222 and an elongated support 210b, which extends through the loops 206b, 208b, and 222.

FIG. 19 illustrates an embodiment of a ring splint 200c that includes two loops 206c and 222c attached to each other and positioned at an angle gamma (γ) to one another and attached to an elongated support 210c.

FIG. 20 illustrates an embodiment of a ring splint 230 that includes a first loop 232, a second, at least partial, loop 234, and an elongated support 236.

In some embodiments of the ring splint, the elongated support is optional, i.e., it is not present on the ring splint.

All references referred to herein are incorporated herein.

What is claimed is:

1. A ring splint comprising:
   a first metal loop;
   a second at least partial metal loop extending away from the first loop at an angle that is at least 45 degrees; and
   a linear elongated support attached to the first loop and the second at least partial loop forming at least one area of attachment,
   the linear elongated support comprising a longitudinal extent extending from a first end near the at least one area of attachment to a point beyond the at least one area of attachment, terminating in a second end that is free from attachment, and having a length and a width, the length being greater than the width,
   the ring splint being adapted to being positioned on a toe such that, when the ring splint is positioned on the toe, the elongated support contacts a plantar surface of the toe.

2. The ring splint of claim 1, wherein the second at least partial loop is a closed loop and is flexible.

3. The ring splint of claim 1, wherein the second at least partial loop extends from the first loop in the form of a spiral.

4. A method of using the ring splint of claim 1, the method comprising:
   positioning the second at least partial loop around a proximal phalanx of a toe;
   positioning the first loop around the intermediate phalanx of the toe; and
   positioning the elongated support against at least a portion of a plantar surface of the toe.

5. A ring splint comprising:
   a first metal loop configured to receive a phalange;
   a second metal loop configured to receive a phalange;
   a third at least partial loop attached to the second loop; and
   a flexible, linear elongated support attached to the first loop at a first area of attachment and the second loop at a second area of attachment,
   the elongated support comprising a longitudinal extent comprising a length and a width, the length being greater than the width,
   the ring splint being adapted to being positioned on a phalange such that, when the ring splint is in position on the phalange, the elongated support is in facing relation with a ventral surface of the phalange.

6. The ring splint of claim 5, wherein the third at least partial loop defines an angle with the second loop that is greater than 30 degrees.

7. The ring splint of claim 5, wherein the third at least partial loop extends from the second loop in the form of a spiral.

8. The ring splint of claim 5, wherein the third at least partial loop extends away from the second loop at an angle of at least 10 degrees.

9. A ring splint comprising:
   a first metal loop configured to receive a phalange;
   a second metal loop configured to receive a phalange; and
   a flexible, linear elongated support attached to the first loop at a first area of attachment and the second loop at a second area of attachment,
   the elongated support comprising a hinge and a longitudinal extent comprising a length and a width, the length being greater than the width,
   the ring splint being adapted to being positioned on a phalange such that, when the ring splint is in position on the phalange, the elongated support is in facing relation with a ventral surface of the phalange.

10. The ring splint of claim 9, wherein the hinge comprises at least one of a living hinge and a spring hinge.

11. The ring splint of claim 9, wherein the hinge comprises a male component mated to a female component.

12. A ring splint comprising:
a first metal loop;
a second metal loop;
an elongated support attached to the first loop at a first area of attachment and the second loop at a second area of attachment, the elongated support comprising
    a linear longitudinal extent comprising a length and a width, the length being greater than the width,
    a first portion comprising a distal surface,
    a second portion comprising a distal surface, and
    a hinge disposed between the first portion and the second portion, the hinge allowing the distal surface of the first portion and the distal surface of the second portion to move toward each other.

13. The ring splint of claim 12, wherein the hinge comprises a male component mated to a female component.

14. A ring splint comprising:
a first metal loop configured to receive a phalange;
a second metal loop configured to receive a phalange; and
a flexible, linear elongated support attached to the first loop at a first area of attachment and the second loop at a second area of attachment,
the elongated support comprising a spring and a longitudinal extent comprising a length and a width, the length being greater than the width,
the ring splint being adapted to being positioned on a phalange such that, when the ring splint is in position on the phalange, the elongated support is in facing relation with a ventral surface of the phalange.

15. The ring splint of claim 14, wherein the spring comprises a first end and a second end, and the elongated support further comprises a first elongate section attached to the first end of the spring, and a second elongate section attached to the second end of the spring.

16. A ring splint comprising:
a first metal loop configured to receive a phalange;
a second metal loop configured to receive a phalange;
a flexible, linear elongated support attached to the first loop at a first area of attachment and the second loop at a second area of attachment,
the elongated support comprising a longitudinal extent comprising a length and a width, the length being greater than the width; and
a third at least partial loop attached to the elongated support,
the ring splint being adapted to being positioned on a phalange such that, when the ring splint is in position on the phalange, the elongated support is in facing relation with a ventral surface of the phalange.

17. A ring splint comprising:
a first metal loop configured to receive a phalange;
a second metal loop configured to receive a phalange;
a flexible, linear elongated support attached to the first loop at a first area of attachment and the second loop at a second area of attachment,
the elongated support comprising a longitudinal extent comprising a length and a width, the length being greater than the width; and
a cushion enveloping at least a portion of the longitudinal extent of the elongated support,
the ring splint being adapted to being positioned on a phalange such that, when the ring splint is in position on the phalange, the elongated support is in facing relation with a ventral surface of the phalange.

18. A ring splint comprising:
a first metal loop configured to receive a phalange;
a second metal loop configured to receive a phalange; and
a flexible, linear elongated support attached to the first loop at a first area of attachment and the second loop at a second area of attachment,
the elongated support comprising a longitudinal extent comprising a length and a width, the length being greater than the width,
the elongated support being removably attached to the first and second loops,
the ring splint being adapted to being positioned on a phalange such that, when the ring splint is in position on the phalange, the elongated support is in facing relation with a ventral surface of the phalange.

19. A ring splint comprising:
a first metal loop configured to receive a phalange;
a second metal loop configured to receive a phalange; and
a flexible, linear elongated support attached to the first loop at a first area of attachment and the second loop at a second area of attachment,
the elongated support comprising a longitudinal extent comprising a length and a width, the length being greater than the width,
the elongated support being repeatedly repositionable on the first and second loops,
the ring splint being adapted to being positioned on a phalange such that, when the ring splint is in position on the phalange, the elongated support is in facing relation with a ventral surface of the phalange.

* * * * *